US008541643B2

(12) United States Patent  
Ring et al.

(10) Patent No.: US 8,541,643 B2
(45) Date of Patent: Sep. 24, 2013

(54) SUPERABSORBENTS, NANOFIBER NONWOVENS FINISHED THEREWITH AND USE THEREOF

(75) Inventors: Horst Ring, Winsen (DE); Roland Harbig, Gams (CH)

(73) Assignee: Schill + Seilacher Aktiengesellschaft (DE)

( * ) Notice: Subject to any disclaimer, the term of this patent is extended or adjusted under 35 U.S.C. 154(b) by 523 days.

(21) Appl. No.: 11/568,608

(22) PCT Filed: Dec. 23, 2005

(86) PCT No.: PCT/EP2005/014017
§ 371 (c)(1),
(2), (4) Date: Nov. 2, 2006

(87) PCT Pub. No.: WO2007/016970
PCT Pub. Date: Feb. 15, 2007

(65) Prior Publication Data
US 2008/0255531 A1     Oct. 16, 2008

(30) Foreign Application Priority Data

Aug. 5, 2005 (DE) .......................... 10 2005 036 992
Nov. 16, 2005 (DE) .......................... 10 2005 054 698

(51) Int. Cl.
*A61F 13/53* (2006.01)
(52) U.S. Cl.
USPC ............................................ 604/368; 604/367
(58) Field of Classification Search
None
See application file for complete search history.

(56) References Cited

U.S. PATENT DOCUMENTS

| 4,043,331 | A |   | 8/1977  | Martin et al. ................. 128/156 |
| 4,354,487 | A | * | 10/1982 | Oczkowski et al. .......... 604/366 |
| 4,429,001 | A | * | 1/1984  | Kolpin et al. ................. 442/340 |
| 4,500,315 | A | * | 2/1985  | Pieniak et al. ................ 604/379 |
| 4,625,001 | A | * | 11/1986 | Tsubakimoto et al. ........ 526/88 |
| 4,666,983 | A | * | 5/1987  | Tsubakimoto et al. ....... 525/119 |
| 4,826,497 | A | * | 5/1989  | Marcus et al. ................ 604/359 |
| 4,855,179 | A | * | 8/1989  | Bourland et al. ............. 442/409 |
| 5,061,259 | A | * | 10/1991 | Goldman et al. ............. 604/368 |
| 5,100,397 | A | * | 3/1992  | Poccia et al. ................. 604/365 |
| 5,147,646 | A | * | 9/1992  | Graham ........................ 424/424 |
| 5,422,169 | A | * | 6/1995  | Roe .............................. 428/212 |
| 5,562,646 | A | * | 10/1996 | Goldman et al. ............. 604/368 |
| 5,599,336 | A | * | 2/1997  | Plischke ...................... 604/368 |
| 5,629,377 | A |   | 5/1997  | Burgert et al. ............... 524/832 |
| 5,714,156 | A | * | 2/1998  | Schmidt et al. .............. 424/404 |
| 5,916,204 | A | * | 6/1999  | Milani .......................... 604/368 |
| 5,990,377 | A | * | 11/1999 | Chen et al. ................... 604/381 |
| 6,103,358 | A | * | 8/2000  | Bruggemann et al. ..... 428/317.9 |
| 6,159,591 | A | * | 12/2000 | Beihoffer et al. ............. 428/327 |
| 6,417,425 | B1| * | 7/2002  | Whitmore et al. ............ 604/367 |
| 6,602,950 | B1| * | 8/2003  | Dentler et al. ............... 524/832 |
| 6,750,262 | B1|   | 6/2004  | Hahnle et al. ................ 521/64 |
| 6,753,454 | B1| * | 6/2004  | Smith et al. .................. 602/41 |
| 6,831,142 | B2|   | 12/2004 | Mertens et al. ............ 526/328.5 |
| 6,872,275 | B2| * | 3/2005  | Ko et al. ...................... 156/181 |
| 7,108,916 | B2| * | 9/2006  | Ehrnsperger et al. ........ 428/403 |
| 7,994,384 | B2| * | 8/2011  | Qin et al. ..................... 604/368 |
| 2002/0039869 | A1| * | 4/2002 | Achille ........................ 442/417 |
| 2004/0133176 | A1| * | 7/2004 | Muthiah et al. .............. 604/368 |
| 2004/0176557 | A1| * | 9/2004 | Mertens et al. ............ 526/328.5 |
| 2004/0186244 | A1|   | 9/2004 | Hatsuda et al. .............. 525/451 |
| 2004/0201117 | A1| * | 10/2004 | Anderson ...................... 264/4.3 |
| 2004/0241333 | A1| * | 12/2004 | Cielenski et al. .......... 427/421.1 |
| 2004/0265387 | A1|   | 12/2004 | Hermeling et al. ............ 424/486 |
| 2005/0003191 | A1| * | 1/2005 | Ehrnsperger et al. ......... 428/403 |
| 2005/0008776 | A1|   | 1/2005 | Chhabra et al. .............. 427/180 |
| 2006/0155254 | A1| * | 7/2006 | Sanz et al. .................... 604/378 |

FOREIGN PATENT DOCUMENTS

| CN | 1466469       | 1/2004  |
| DE | 19909214      | 3/1999  |
| DE | 19958697      | 12/1999 |
| DE | 10202839      | 1/2002  |
| WO | WO 01/27365   | 4/2001  |
| WO | WO 2005/005704| 1/2005  |

OTHER PUBLICATIONS

Ullmanns Encyclopedia of Industrial Chemistry, Sulfuric Acid & Sulfur Trioxide to Tetrahydrofuran, Superabsorbents, 6th Edition, vol. 35, pp. 73, 80, 86 and 89, 2003).
Hansen et al., "Water Absorption and Mechanical Properties of Electrospun Structured Hydrogels", Journal of Applied Polymer Science, vol. 95, pp. 427-434 (2005).

(Continued)

*Primary Examiner* — Melanie Hand
*Assistant Examiner* — Paula Craig
(74) *Attorney, Agent, or Firm* — Hayes Soloway P.C.

(57) ABSTRACT

The invention relates to a superabsorbent powder consisting of polymer particles which have a core swelling in the presence of water and a superficially postcured shell, in which the powder is a screening fraction of such polymer particles which have not been crushed after the superficial postcure of their shell. This superabsorbent powder is especially suitable for the finishing of textile webs made of super-fine fibers or filaments with a diameter of less than 10 μm, in particular for the finishing of sanitary products. There is further proposed the use of a nanofiber nonwoven, finished with a superabsorbent for the absorption and retention of hydrophilic fluids, for the absorption and/or sustained release of at least one of the following fluids: body fluids, sweat of humans and animals, water, including cooling water, condensation water and water vapor, chemicals, including agrochemicals and pesticides, pharmaceuticals, biocides, germicides and fungicides, diagnostics, fire protection and fire extinguishing agents, cleaning agents, hydraulic fluids, heating and cooling fluids, sewage, including radioactively contaminated fluids, perfumes.

20 Claims, No Drawings

(56) References Cited

OTHER PUBLICATIONS

Korean Official Action dated May 16, 2011, Appln. No. 2008-7005433, (3 pgs).

Chinese Official Action dated Mar. 17, 2010.
International Preliminary Report, PCT/IPEA/409, 7 pages, Dec. 23, 2005.

* cited by examiner

SUPERABSORBENTS, NANOFIBER NONWOVENS FINISHED THEREWITH AND USE THEREOF

This is a national stage application of PCT/EP2005/014017 filed Dec. 23, 2005, and claims priority to German application Nos. 10 2005 036 992.8 filed Aug. 5, 2005 and 10 2005 054 698.6 filed Nov. 16, 2005.

The invention relates to a superabsorbent powder consisting of polymer particles which have a core swelling in the presence of water and a superficially postcured shell, its use for the finishing of textile webs made of super-fine fibers or super-fine filaments having a diameter of less than 10 μm, as well as to the use of a nanofiber nonwoven, finished with the superabsorbent for the absorption and retention of hydrophilic fluids, for the absorption and/or release of one or more fluids or mixtures of fluids.

"Superabsorbents" are to be understood as polymer materials which have the ability of absorbing water or other fluids up to a thousand times their mass, thereby swelling to form a gel. As the uptake and retention capability of the superabsorbents is subject to a rapid and strong limitation due to the "gel blocking" effect, the agglutinating of the superabsorbent particles which have started to swell or are fully swollen up, various methods of a superficially occurring postcure of the superabsorbent particles have already been suggested, resulting in a gradient of the cross-linking degree of the particles which increases inside out, i.e. a core having a lower cross-linking degree and a shell having a higher cross-linking degree. Modified superabsorbents of this kind and methods of their manufacture are known from *Ullmanns Encyclopedia of Industrial Chemistry,* 6th Ed., Vol. 35, pp. 73 ff., 2003, just as their use for the finishing of sanitary products such as diapers and other incontinence products, sanitary napkins and wound dressings.

According to studies, approximately 15 million in Western Europe and about the same number of people in the USA suffer from urinary incontinence. This disturbance of health can be found with women 10 times more frequently than with men. Approximately 25% of the women at the age of 30 to 59 years are at least temporarily incontinent. Even 10 to 20% of the younger women at the age of about 20 years are affected, too. More than 5.2 billion pieces of incontinence products such as diapers for adults are used in Western Europe every year. In the USA the annual expenses for incontinence products are estimated at more than 16.4 billion US dollars, about 35% of which accruing in nursing homes. This results in the big social and economic importance of the development of improved superabsorbents specifically adapted to textile webs, in most cases nonwovens, which are used for such incontinence products.

Incontinence products primarily have the function to take up urine, firmly absorb and effectively bind it. At the same time, moisture is to be kept away from the skin and developing odors are to be suppressed. This is achieved by a multi-ply structure made up of a foil acting as a liquid barrier towards outside, various nonwoven webs for controlling the fluid distribution, and superabsorbents for a reliable fluid absorption.

Apart from this technical functionality, a certain wearing comfort, good fit, discretion (channels of distribution, volume, crackling/rustling) and a hygienic manageability are desired.

Already today, incontinence products make it possible for less affected persons to live a mostly normal everyday life. Nevertheless, the mobility is limited and the abidance is confined to an environment with sanitary infrastructure, which in the end has an influence on the social and work-related situation, as well.

In the case of a more pronounced incontinence these impairments will especially become evident, although it is possible to master technical problems with the materials available today and with constructions of incontinence products, but to the account of the wearing comfort, fit, discretion and handling.

As incontinence is a social taboo subject, the social/psychological component of this disturbance of health has a special importance in particular for younger women and may lead right up to isolation, loneliness and loss of self-confidence and autonomy.

Materials of a new type for the use in novel incontinence products can produce relief here, which especially account for the need for discretion by a small volume, low thickness, reduced noise and a high wearing comfort.

From U.S. Pat. No. 5,629,377 it is already known to use superabsorbent powders made of superficially postcured polymer particles for the finishing of diapers and other incontinence products. It has turned out, however, that commercially available superabsorbent powders in combination with super-fine fiber nonwovens, which are preferred because of a preferably dry skin surface of the user of these products, are still not optimal. It was not possible to process them in a problem-free manner, they were not properly integrated in the nonwoven structure and oozed out of the nonwoven structure upon wetting.

"Nanofiber nonwovens" are supposed to be nonwovens made of textile fibers having a diameter of less than 10 μm, preferably less than 1 μm. Nanofiber nonwovens and methods for their manufacturing are known, for instance, from the U.S. Pat. No. 4,043,331 and the International Patent Application WO 01/27365. The nanofiber nonwovens known from prior art are not finished with superabsorbents, but for their part were used for the finishing of sanitary products and wound dressings.

The invention is based on the object to provide a superabsorbent powder which is especially suitable for combining it with super-fine fiber nonwovens, while the use of such powder in the finishing of textile webs such as sanitary products results in more economical production options, as well as to provide application ways for the super-fine fiber nonwovens finished with the superabsorbent for the absorption and retention of hydrophilic fluids, in which the advantageous properties of the nanofiber nonwovens finished in this way manifest particularly clearly in economical, ecological or technical terms.

This object is achieved according to the invention with a superabsorbent powder of the type initially mentioned in that the powder is a screening fraction of such polymer particles which have not been crushed after the superficial postcure of their shell.

It has turned out surprisingly that the customary superabsorbent powders failed even if they had in principle an optimum grain size and a suitable grain size distribution for a particular super-fine fiber nonwoven, because they have been crushed several times in the course of their manufacture, even after their postcure, whereby the core/shell structure of the particles was damaged and the gel blocking effect began anew. This is the reason why optimum water absorption and water retention values could not be achieved with super-fine fiber nonwovens, although acceptable results could be achieved with "normal" or coarser fiber nonwovens with the same customary superabsorbent powders. Only when carefully screened, uncrushed particles as superabsorbent powders were selected and used in combination with super-fine fiber nonwovens, the desired optimum water absorption and water retention values appeared. This not only applies to the absorption and retention of water, but also to the absorption and retention of other hydrophilic fluids.

If the employed screening fraction shows a grain size distribution of d50=55 to 100 μm and d100=100 to 150 μm, the best results are achieved according to the invention in combination with nanofiber nonwovens. The specification "d50=55 μm" means that 50% by weight of the particles have a grain size of up to 55 μm, actually 55 μm or less, and "d100=100 μm" means that 100% by weight of the particles have a grain size of up to 100 μm, i.e. no particle is larger than 100 μm.

It is preferred that the polymer, of which the superabsorbent particles are consisting, is a (meth)acrylate or a (meth) acryl copolymer; it is particularly preferred that the polymer is sodium polyacrylate.

According to the invention, the superabsorbent powder of the selected screening fraction is used for the finishing of textile webs made of super-fine fibers or super-fine filaments having a diameter of less than 10 μm. The fibers or filaments preferably have a diameter of less than 1 μm. Such super-fine fibers are referred to as microfibers or nanofibers.

The use of the superabsorbent powders for the finishing of nanofiber nonwovens, in particular of those made of electrostatically spun nanofibers, has turned out to be particularly advantageous, which will be explained in detail below.

The fibers or filaments preferably consist of a thermoplastic and hydrophilic or hydrophilized polymer which is melt-spinnable with polyurethane being particularly preferred.

The superabsorbent powder according to the invention is preferably used for the finishing of sanitary products which are made of textile webs. It is particularly preferred that, according to the invention, diapers and other incontinence products, sanitary napkins and wound dressings are finished so as to be fluid absorbing.

Thus, a preferred result of the use according to the invention is an elastic, superabsorbent nonwoven of nanofibers for the use in novel sanitary articles, in particular in incontinence products with improved wearing comfort, safe odor binding and enhanced discretion. The sanitary article consists of a nonwoven fabric of thermoplastic polyurethane, in which the superabsorbent powder made of polyacrylate having a specific grain size distribution and a specific postcure treatment is mechanically integrated. The proportion of specific superabsorbent may amount up to 85% by weight of the total weight of the finished textile piece.

The nanofiber nonwoven finished with the superabsorbent according to the invention for the absorption and retention of hydrophilic fluids is preferably used for the absorption and/or sustained release of at least one of the following fluids: body fluids, sweat of humans and animals, water, including cooling water, condensation water and water vapor, chemicals, including agrochemicals and pesticides, pharmaceuticals, biocides, germicides and fungicides, agents for use in diagnostics, fire protection and fire extinguishing agents, cleaning agents, hydraulic fluids, heating and cooling fluids, sewage, including radioactively contaminated fluids, perfumes.

For the uptake and/or sustained release of body fluids the nanofiber nonwoven according to the invention is preferably used as an incontinence article, diaper, sanitary napkin, wound dressing, cooling compress, sanitary tissue, cosmetic pad or bed inlay or as a part of the aforementioned goods.

For the uptake and/or sustained release of sweat of human or animal origin, the nanofiber nonwoven according to the invention preferably is used as a sweat absorbing padding material for shoes, garments, headgears, headbands, gloves, upholstered furniture, vehicle seats, saddles, bed linen, bedspreads, horse blankets, sports goods or pieces of sports equipment.

For the uptake and/or sustained release of water, including cooling water, condensation water and water vapor, the nanofiber nonwoven according to the invention preferably is used as a wipe, floor cloth, casualty protection mat, camping mat, tarpaulin, wet cloth, drying cloth, polishing cloth, cleaning cloth or washleather or as a part of the aforementioned goods.

In the field of construction the nanofiber nonwoven according to the invention is used for the uptake and/or sustained release of water, including cooling water, condensation water and water vapor, preferably as a floor covering or wall covering, parquet underlay sheeting, roof underlay sheeting, fire protection mat, leakage protection mat, mat for the lining of damp rooms, tents, vehicles, tanks or containers or as a part of the aforementioned goods.

A further preferred use of the nanofiber nonwoven according to the invention is possible as a filter material, packaging material, sheathing, insulating material or sealing material or as a part of the aforementioned goods. Examples of preferred uses are the packaging of dangerous goods, the sheathing of tubes and conduits, of pipelines, of electric cables, including communication cables and power supply cables, and of all objects in which fluids of the aforementioned type are stored or transported, develop in the form of condensation water and water vapor, or may escape in consequence of leakages or accidents.

For the uptake and/or sustained release of chemicals, including agrochemicals and pesticides, the nanofiber nonwoven according to the invention preferably is used as a geo web, drainage mat, agro web or as a nonwoven for the sustained release of pharmaceuticals, chemicals, fertilizers or pesticides. In this field of application, nonwovens may be involved which are spread out across large areas in greenhouses or across the soil over fields, acres and plantations, in order to either imbibe the cited agents or release them with some delay. An important application field for the nanofiber nonwovens according to the invention are ecological disasters in which large amounts of environmentally detrimental fluids have escaped, for instance in consequence of traffic accidents.

In the application possibilities, proposed according to the invention, of the nanofiber nonwovens finished with the superabsorbent, the high water and fluid retention capability and the high speed of the water and fluid uptake with a concurrent, particularly slow and retarded (re-)release of the absorbed fluid amounts manifest at advantage. Due to this, even larger amounts of spilled fluids can be taken up and eliminated in a very short time.

On the other hand, the nonwovens can be preventively employed throughout those places where leakages are to be feared and where water, but also poisonous, corrosive, acidic, alkaline or environmentally hazardous fluids may escape from conduits, containers, packagings, tanks, vehicles, industrial plants etc.; the emerging fluids will immediately be taken up by the nonwovens with which the conduits etc. have been sheathed or packed or lined, and are absorbed due to a wicking effect which begins very rapidly.

The advantages of the invention will be explained in the following by example of sanitary products based on textile webs, but are not construed to be limiting:

1. Improved Discretion

The reason for the thickness and bulkiness of incontinence products is primarily due to the fact that superabsorbent powder (SAP) swells upon contacting water and the particles agglutinate, whereby further absorption of water is made more difficult or prevented (gel blocking). In order to avoid gel blocking, it was common practice hitherto to use SAP always in a mixture together with short cellulose fibers (pulp), which are supposed to keep the particles apart. In doing so, the proportion of SAP may amount to 50% at the maximum. Pulp has a very low density, is therefore very bulky and considerably blows up the volume of the amount of SAP/pulp which is needed for the uptake of fluid.

In order to avoid these disadvantages and to be able to do without pulp, while ensuring at the same time a large surface area as with SAP, there have been made various attempts to use the superabsorbent not in the form of a powder, but in another make-up, for instance as foam, fiber nonwoven or in the form of fibers and nonwovens coated with superabsorbents. These constructs, however, could not be used because of serious disadvantages such as a loss of strength after wetting, brittleness/fragility in the dry state or a marked anisotropy of the wetting behavior.

The novel approach of the material according to the invention now is to incorporate the individual particles of the superabsorbent powder with a defined grain size distribution in an elastic nonwoven structure in such a manner that the particles are spatially separated from each other, so that they are wetted all-over by contact with water and are able to freely swell in all three dimensions. Due to the elasticity of the nonwoven matrix gel blocking is being prevented, as the nonwoven matrix yields in view of the increasing space requirements during swelling of the superabsorbent, thereby the particles are being largely kept away from each other.

2. Improved Wearing Comfort

Due to the elastic nonwoven structure with a high proportion of superabsorbents, it is possible to replace bulky SAP/pulp mixtures which are common at present and to avoid the disadvantages of customary incontinence articles. The thickness is reduced to $1/10$. It is due to the smoothness, elasticity and the low thickness of the material according to the invention that the designer of incontinence articles has all options to unite a clothing-like wearing comfort with discretion and technical performance.

3. Simplified Manufacturing Process of the Sanitary Articles

Further, a simplification of the diaper manufacturing process is achieved, by expensive conditioning plants for pulp and plants for mixing SAP with pulp arranged upstream of a diaper machine are replaced with a placement of the elastic, superabsorbent nonwovens in the form of webs, strips or coil goods. In addition, any diaper construction is simplified, because one can do without construction elements such as tissue and corewrap. The diaper structure is reduced to e.g. an elastic, breathing membrane, onto which the object according to the invention (elastic and absorbing nonwoven) is applied during the manufacturing process, and the covering with distributing and/or coating nonwoven. It may happen already during the manufacturing process of the material according to the invention that it is applied onto a membrane or foil as a carrier material and covered in the subsequent process step with conventional nonwovens. In the so obtained composite, the membrane or foil correlates to a customary back sheet, the material according to the invention to a customary absorbent core and the coating nonwoven to the distribution layer or top web, or with both in case of a suitable construction.

4. Odor

Any conventional approaches for the odor binding assume that volatile, mostly amine-type compounds as odor carriers are formed by the bacterial decomposition of urine components. According to this, one tries to put a stop to the propagation and activity of microorganisms by adjustment of the neutralization level of the superabsorbents, and the use of pH buffers or bacteriostatic agents. Here, the use of bacteriostatic agents or even bactericides is highly controversial because of the associated risks to produce allergies.

Based on the fact that urinary odor substantially is the odor of gaseous ammonia which is formed by the enzymatic decomposition of urea, and that the active enzyme indeed is used by microorganisms for the metabolic digestion of urea, but the effectiveness and the occurrence of the enzyme is not bound to living cells, the novel approach for the solution of this problem with customary incontinence articles is not to combat microorganisms, but to block the effectiveness of ureolytic enzymes by specific enzyme blockers.

Substituting harmless enzyme blockers for customary allergy-producing cytotoxins such as bactericides does not limit technologies for binding odor to patients or cases where a corresponding balance of benefit/risk is available, but allows a broad application to the improvement of the quality of life of incontinent people.

The enzyme blockers may be added to the spinning mass during the manufacture of the elastic nonwoven and be active at the surface of the fibers after diffusion, or they may be subsequently applied on the fiber surface in the form of an impregnation.

5. Textile Webs

From literature, for instance from U.S. Pat. No. 4,043,331 it is known that polymers from solution can be processed to nonwovens of endless filaments by means of the electrospinning technology. Electrospinning is still a not very widespread, predominantly experimental technology for the production of nonwoven webs. Like no other nonwoven laying technology, however, it offers the possibility to produce endless filaments from different polymers, also elastomers, which have diameters in the nanometer range, and to lay down in the form of a kind of spun nonwoven and to mechanically incorporate particles such as grains or microcapsules (filled with active agents, aromatic substances et al., activatable by water or temperature) in the nonwoven structure during the spinning process. In addition, there is the possibility to add active agents such as enzymes, enzyme blockers, vitamins, detergents, wetting agents et al. to the spinning solution, which due to diffusion to the surface of the spun fibers can develop their activity there.

L. M. Hansen et. al. write in *Journal of Applied Polymer Science*, Vol. 95, pp. 427-434 (2005) about a nonwoven made of thermoplastic polyurethane and produced by an electrospinning method, which is filled with a superabsorbent in the form of modified starch from the company Grain Processing Corp., Muscatine, Iowa, with the trade name "Waterlock". This material already has interesting properties which, however, do not fulfill the requirements in terms of specific absorption, speed of the fluid uptake and the maximum filling level with absorber as a substitute for an absorbent core in sanitary articles.

In expectation to be able to fulfill the requirements when the modified starch (Waterlock) of the existent material is replaced with polyacrylates, as they are commonly used as superabsorbents in sanitary articles, commercial superabsorbent powder was crushed down to a grain size which appeared to be needed for the incorporation in said nanofiber nonwoven; with this material, a nano-nonwoven was produced which contained a superabsorbent. As expected, an absorption behavior was observed which was improved compared to nonwovens filled with modified starch (Waterlock), but filling levels of more than 50% could not render a measurable improvement of the specific absorption due to gel blocking.

Surprisingly it was found that superabsorbent particles of sodium polyacrylate with suitable grain size, which were not manufactured by crushing customary superabsorbent powders, but obtained as a screening fraction of superficially postcured particles, give the overall construct of preferably polyurethane nonwoven and superabsorbent distinctly superior properties, despite a basically sustained absorption in comparison with customary superabsorbent powder. Only the use of superficially postcured superabsorbent powder of polyacrylate or another suitable copolymer with intact core/shell structure and a suitable grain size distribution allows a rapid uptake and distribution of the fluid and a high specific absorption concomitantly with a high filling level of up to approx. 85% of the superabsorbent nonwovens consisting of thermoplastic polyurethane and superabsorbent powder with diameters of the individual filaments in the nanometer to micrometer range.

The invention will be explained in more detail below according to examples:

Test Methods

A. Teabag Absorption Test (Tb)

The "teabag" absorption test gives information about the resistance-less fluid absorption. A defined amount of a SAP sample is filled in a commercial teabag; the teabag is immersed for 30 minutes in excessive 0.9% solution of sodium chloride and is taken out; after this the bag is left for 10 minutes in order to drip off.

The Tb value in [g/g] is the ratio between the absorbed amount of water and the original amount of SAP.

B. Water Retention Test

The test shows the water retention of the swollen SAP sample. The swollen teabag from the Tb test is put into a centrifuge and is centrifuged for 3 minutes with an acceleration of 250 g.

The CRC value in [g/g] is the ratio between the retained amount of water and the original amount of SAP.

C. Vertical Wicking Effect

The test gives information on the speed and the preferential direction of the spreading of the water absorption. An adhesive tape of the size of 10×1 cm with an SAP sample sticking thereon is marked at equal distances of 1 cm and perpendicularly immersed in a 0.9% solution of NaCl as far as to the first 1 cm mark; the fluid extension is compensated by adjusting the strip with respect to the mark. The time is measured at which the run of 1, 2, 3, 4 and 5 cm is reached by the upward movement of the solution on the tape.

Results

Nonwovens of thermoplastic polyurethane and various absorbing materials with different charge amounts were manufactured according to the electrospinning method on a laboratory spinning facility or pilot spinning facility and subjected to the above described tests.

In the experiments 3, 4, 6 and 7 according to the invention, superficially cross-linked sodium polyacrylate powder with a core/shell structure with a grain size distribution of the screening fraction of d50 approx. 100/μ and d100 approx. 150μ, Tb approx. 38 g/g and CRC approx. 22 g/g was used as superabsorbent (SAP).

Comparison experiment 5 was carried out with mechanically crushed (and therefore not according to the invention) and subsequently screened superabsorbent (SAP) with a grain size distribution of the screening fraction of d50 approx. 55μ and d100 of 100μ, Tb approx. 38 g/g, CRC approx. 22 g/g.

Commercially available SAP, in grain size fractions as they are usual today in customary sanitary articles, turned out to be too coarse. It was not possible to process them in a trouble-free manner, they were not perfectly integrated in the nonwoven structure and oozed out of the nonwoven structure upon wetting. This is why first pilot experiments with commercial SAP types were ceased already.

The results of the experiments are summarized in Table 1.

It turned out that by the use of superficially cross-linked sodium polyacrylate powder with a core/shell structure with filling levels of about 50% and a grain size of d50=100μ, d100=150μ the speed of the water uptake could be lowered from 450 sec. to 80 sec. and the water uptake could be augmented from 29 g/g to 40 g/g and from 16 g/g to 22 g/g, respectively. With a filling level of 50%, gel blocking can still not be ascertained, the Tb and CRC values rather achieving the theoretical values of pure SAP. A sample with the same composition which was produced on a larger pilot spinning facility showed comparably good results and confirms the reproducibility (experiment 6).

It further turned out in experiment 5 that any damage of the postcured shell of the SAP particles by mechanical crushing and a concomitant increase of the proportion of smaller grain sizes in the screening fraction of the SAP has a detrimental effect on the speed of the fluid uptake and fluid distribution in the nonwoven.

The experiments also demonstrated that only the combination of an elastic nonwoven structure with superficially postcured SAP with intact core/shell structure and suitable grain size results in the specifically desired markedness of the essential quality features such as speed of the fluid uptake and fluid distribution and absorption capability (Tb, CRC). It was surprisingly found that it is not an especially fine powder which shows the best effect, as was expected because of the fine nonwoven structure, but that an optimum of the particle size exists, which is distinctly coarser than the dimensions of the nonwoven structures.

TABLE 1

Absorption Behavior of various Nonwoven Samples in dependency of the Absorbent Material and the Filling Level

| No. | Absorbent Material | Filling Level | Vertical Wicking 4 cm [sec] | Tb [g/g] | CRC [g/g] |
|---|---|---|---|---|---|
| 1 | Waterlock | 50% | 450 | 29 | 16 |
| 2 | " | 70% | 480 | 24 | 14 |
| 3 | SAP (core/shell) | 40% | 260 | 41 | 22 |
| 4 | " | 50% | 80 | 40 | 18 |
| 5 | SAP (finer grain) | 50% | 170 | 41 | 21 |
| 6 | SAP (core/shell) (*) | 50% | 90 | 50 | 22 |
| 7 | SAP (core/shell) | 75% | 270 | 29 | 16 |

(*) pilot spinning facility

The invention claimed is:

1. A process for the finishing of textile webs comprising combining a textile web with a superabsorbent powder wherein the superabsorbent powder comprises polymer particles having a core swelling in the presence of water and a superficially postcured shell; wherein the superabsorbent powder is surface cross-linked to form the superficially postcured shell and thereafter screened to a screening fraction of the polymer particles with an intact core/shell structure after the superficial postcure of their shell, wherein the screening fraction of said powder has a grain size distribution of d50=55 to 100 μm and d100=100 to 150 μm, and wherein said textile web is made from a nanofiber nonwoven formed of super-fine fibers or super-fine filaments having a diameter of less than 10 μm.

2. The process according to claim 1, wherein products made of electrostatically spun nanofibers are used as said textile webs.

3. The process according to claim 1, wherein the fibers or filaments comprise a thermoplastic and hydrophilic or hydrophilized polymer which is melt-spinnable.

4. The process according to claim 3, wherein the fibers or filaments comprise polyurethane.

5. The process according to claim 1, wherein the textile webs constitute a sanitary product.

6. The process according to claim 5, wherein said sanitary product is selected from the group consisting of an incontinence product, a sanitary napkin and a wound dressing.

7. The process of claim 1, wherein said polymer is a (meth)acrylate or a (meth)acryl copolymer.

8. The process of claim 1, wherein said polymer is sodium polyacrylate.

9. A process for finishing a nanofiber nonwoven for the absorption and retention of hydrophilic fluids comprising combining said nonwoven with a superabsorbent powder consisting of polymer particles which have a core swelling in the presence of water and a superficially postcured shell, wherein said powder is surface cross-linked to form said superficially postcured shell and thereafter screened to a screening fraction of such polymer particles with an intact core/shell structure after the superficial postcure of their shell, said screening fraction of said powder having a grain size distribution of d50=55 to 100 μm and d100=100 to 150 μm, and wherein said nanofiber nonwoven is formed of super-fine fibers or super-fine filaments having a diameter of less than 1 μm so as to allow at least one of the following fluids to be uptaken by and/or sustainedly released from said nanofiber nonwoven:
- body fluids,
- sweat of humans and animals,
- water, including cooling water, condensation water and water vapor,
- chemicals, including agrochemicals and pesticides,
- pharmaceuticals, biocides, germicides and fungicides,
- diagnostics,
- fire protection and fire extinguishing agents,
- cleaning agents,
- hydraulic fluids,
- heating and cooling fluids,
- sewage, including radioactively contaminated fluids,
- perfumes.

10. The process according to claim 9, wherein said nanofiber nonwoven is either one of an incontinence article, diaper, sanitary napkin, wound dressing, cooling compress, sanitary tissue, cosmetic pad or bed inlay or a part of the aforementioned goods.

11. The process according to claim 9, wherein said nanofiber nonwoven is a sweat absorbing padding material for shoes, garments, headgears, headbands, gloves, upholstered furniture, vehicle seats, saddles, bed linen, bedspreads, horse blankets, sports goods or pieces of sports equipment.

12. The process according to claim 9, wherein said nanofiber nonwoven is either one of a wipe, floor cloth, casualty protection mat, camping mat, tarpaulin, wet cloth, drying cloth, polishing cloth, cleaning cloth or washleather or a part of the aforementioned goods.

13. The process according to claim 9, wherein said nanofiber nonwoven is either one of a floor covering or wall covering, parquet underlay sheeting, roof underlay sheeting, fire protection mat, leakage protection mat, mat for the lining of damp rooms, tents, vehicles, tanks or containers or a part of the aforementioned goods.

14. The process according to claim 9, wherein said nanofiber nonwoven is either one of a filter material, packaging material, sheathing, insulating material or sealing material or a part of the aforementioned goods.

15. The process according to claim 9, wherein said nanofiber nonwoven is either one of a geo web, drainage mat, agro web or nonwoven for the sustained release of pharmaceuticals, chemicals, fertilizers or pesticides.

16. The process according to claim 9, wherein the nonwoven is manufactured of electrostatically spun nanofibers.

17. The process according to claim 9, wherein the fibers or filaments of the nonwoven comprises a thermoplastic and hydrophilic or hydrophilized polymer which is melt-spinnable.

18. The process according to claim 17, wherein the fibers or filaments comprise polyurethane.

19. The process of claim 9, wherein said polymer is a (meth)acrylate or a (meth)acryl copolymer.

20. The process of claim 9, wherein said polymer is sodium polyacrylate.

* * * * *